United States Patent
O'Leary et al.

(10) Patent No.: US 7,441,755 B2
(45) Date of Patent: Oct. 28, 2008

(54) DEVICE FOR DISPENSING ACTIVE VOLATILE LIQUID

(75) Inventors: Nicholas O'Leary, Slough (GB); Lyse Tranzeat, Melun (FR)

(73) Assignee: Firmenich SA, Geneva (CH)

( * ) Notice: Subject to any disclaimer, the term of this patent is extended or adjusted under 35 U.S.C. 154(b) by 854 days.

(21) Appl. No.: 11/008,584

(22) Filed: Dec. 9, 2004

(65) Prior Publication Data

US 2005/0140032 A1 Jun. 30, 2005

Related U.S. Application Data

(63) Continuation of application No. PCT/IB03/02721, filed on Jul. 10, 2003.

(60) Provisional application No. 60/394,721, filed on Jul. 10, 2002.

(30) Foreign Application Priority Data

Jul. 16, 2002 (WO) ................. PCT/IB02/02858

(51) Int. Cl.
*B01F 3/04* (2006.01)
(52) U.S. Cl. ............... 261/104; 261/107; 261/DIG. 88; 239/44
(58) Field of Classification Search ............ 261/104, 261/107, 119.1, DIG. 65, DIG. 88; 239/44, 239/45; 422/4
See application file for complete search history.

(56) References Cited

U.S. PATENT DOCUMENTS

| 3,587,968 | A | * | 6/1971 | Hennart et al. ............... 239/47 |
| 4,323,193 | A | * | 4/1982 | Compton et al. ............. 239/44 |
| 4,419,326 | A | * | 12/1983 | Santini ......................... 422/4 |
| 4,753,389 | A | * | 6/1988 | Davis ........................... 239/6 |
| 5,932,204 | A | * | 8/1999 | Joshi ......................... 424/76.1 |

FOREIGN PATENT DOCUMENTS

| EP | 0 194 017 | 9/1986 |
| EP | 0 381 529 | 8/1990 |
| EP | 0 462 605 A2 | 12/1991 |
| EP | 0 669 137 A1 | 8/1995 |
| WO | WO 98/16262 | 4/1998 |
| WO | WO 01/56619 A1 | 8/2001 |

* cited by examiner

*Primary Examiner*—Scott Bushey
(74) *Attorney, Agent, or Firm*—Winston & Strawn LLP

(57) ABSTRACT

The present invention relates to the field of perfumery and more precisely it concerns a device, and the consumer articles associated therewith, for dispensing an active composition in the surrounding space. The device includes an active liquid having a specific volatility, a reservoir holding a part of the active liquid, a lid and a wick-emanator superstructure having a wicking part and an emitting part, the latter having an evaporative surface directly exposed to the surrounding space, and a specific absorbency and weight per unit of the evaporative surface.

12 Claims, 3 Drawing Sheets

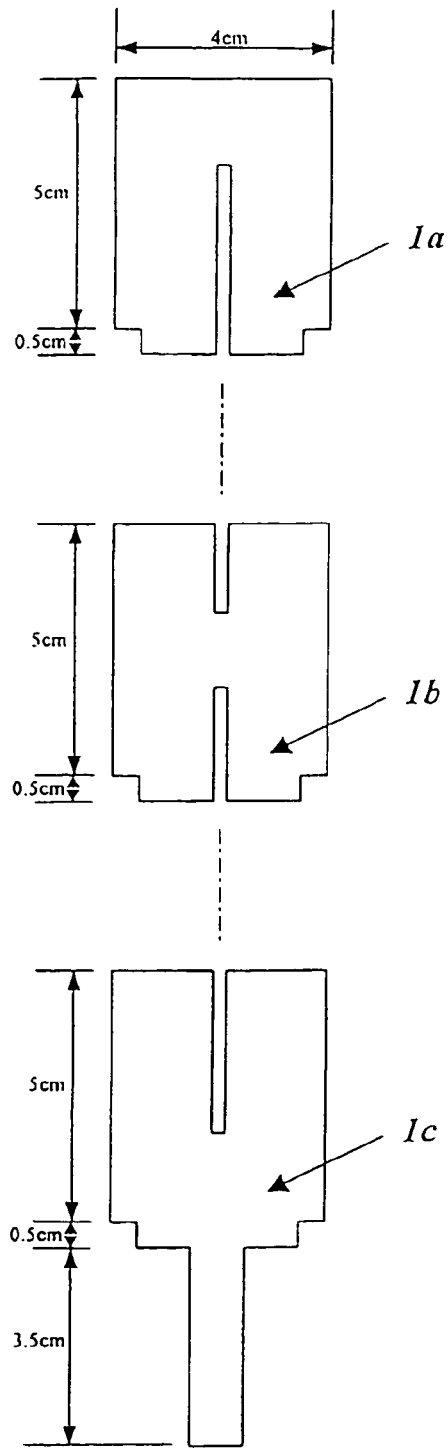
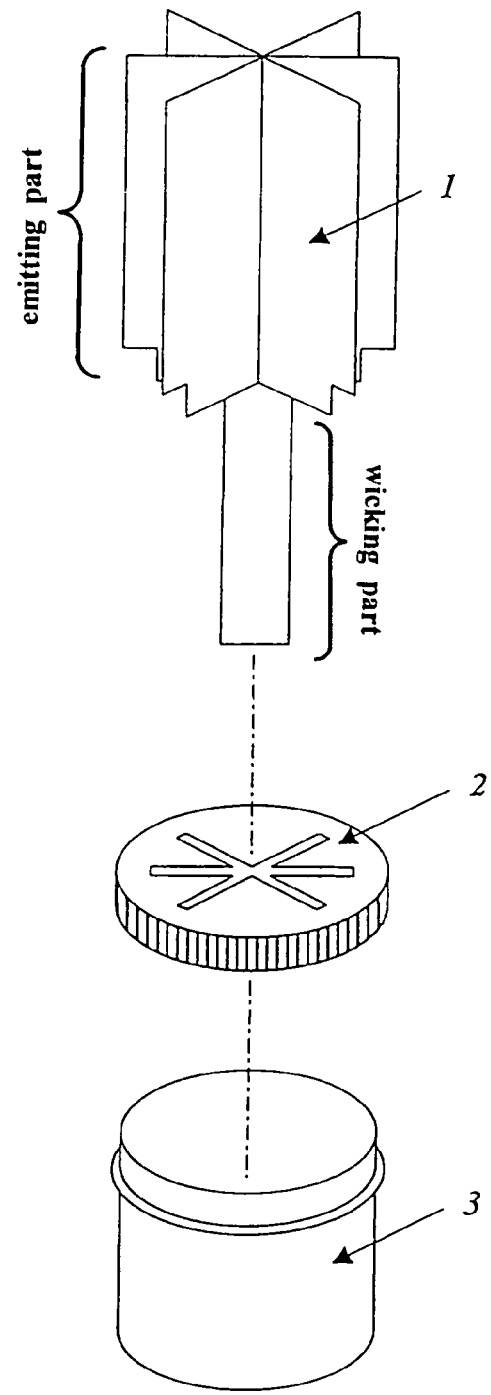
Figure 1
Figure 2

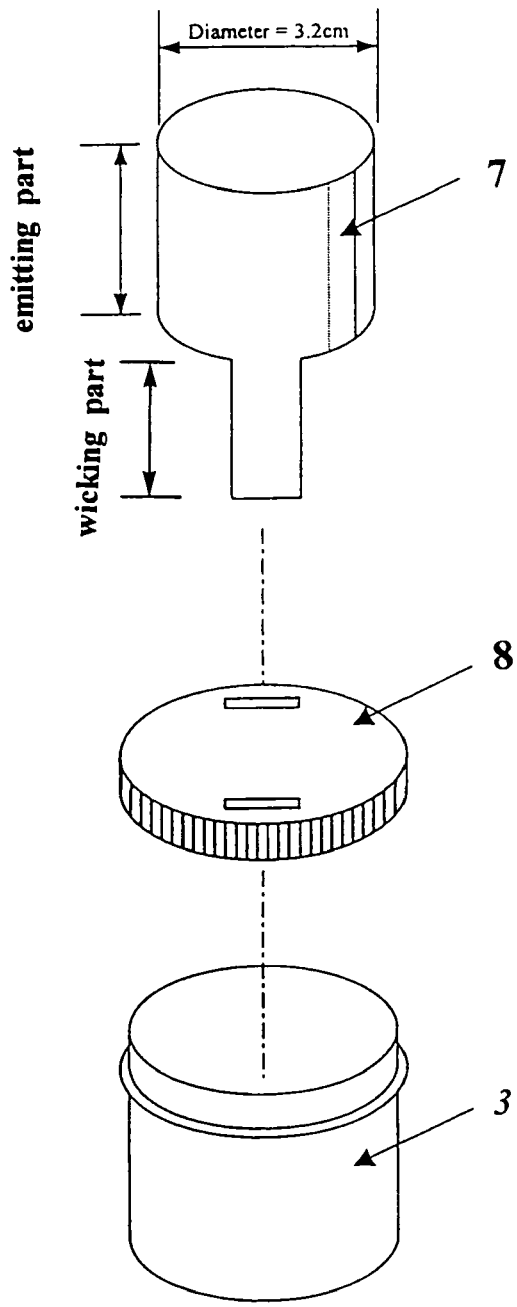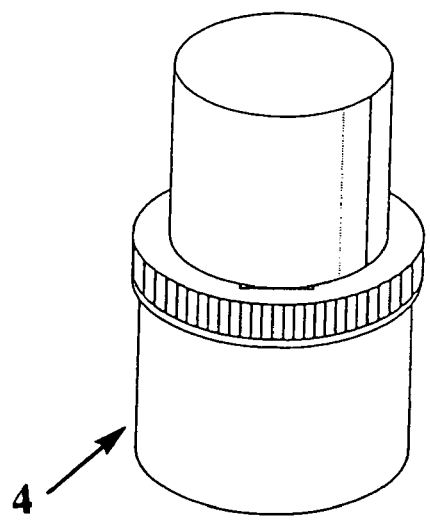
Figure 6
Figure 5

DEVICE FOR DISPENSING ACTIVE VOLATILE LIQUID

CROSS-REFERENCE TO RELATED APPLICATIONS

This application is a continuation of International application PCT/IB2003/002721 filed Jul. 10, 2003, and claims the benefit of U.S. provisional application No. 60/394,721 filed Jul. 10, 2002, the entire content of each of which is expressly incorporated herein by reference thereto.

TECHNICAL FIELD

The present invention relates to the field of perfumery and more precisely it concerns a device and consumer articles associated therewith for dispensing an active volatile liquid in the surrounding space at an approximately constant rate over the lifetime of the device. The device comprises an active liquid, having a specific volatility, a reservoir holding a part of the active liquid, a lid and a wick-emanator superstructure composed of a wicking part and an emitting part, the latter having an evaporative surface directly exposed to the surrounding space, and a specific absorbency and weight per unit of the evaporative surface.

BACKGROUND

Devices for dispensing an active liquid in the surrounding space have been known for a long time. One type device is the so-called wick-based device, which comprises a reservoir, a wick and an emanating body from which the active liquid evaporates.

The main problem of such wick-based devices is the difficulty to achieve a controlled release in the surroundings of the active liquid in order to avoid that the evaporation of the active liquid is too quick or too slow.

The various wick-based devices disclosed in the prior art, and described as solving the above-mentioned problem, can be divided in several categories. Each category is characterized by the fact that the device achieves a controlled release by:

i) the use of special films or occluding systems which enwrap the emanating body;
ii) the use of a cover means which allows to regulate, over the lifetime of the device, the surface of the emanating body from which the active liquid can evaporate (i.e. the evaporative surface); or
iii) the use of an electrically powered assistance such as heating or a fan.

However, all these devices are complex to realize and require additional elements to the devices.

Moreover, with the exception of the electrically assisted devices, the other devices require, in general, the use of an aqueous solution or emulsion of the active liquid, thus implying the use of large amounts of liquid and of surfactants which may be detrimental to the effective releasing performance of the device.

To the best of our knowledge, there is no disclosure, nor suggestion, in the prior art of a device allowing to control the release of the active liquid by using a specific liquid and an emanating body having a specific absorbency and weight per unit of its surface of evaporation.

SUMMARY OF THE INVENTION

The present invention now provides a device for dispensing an active liquid in the surrounding space with essentially linear performance, i.e. at approximately constant rate, without requiring films covering the emanating body, or electrically powered devices. This was achieved by providing a device comprising a specific type of active liquid, composed of materials having a selected vapor pressure, and having a specific type of emanating body.

Therefore, the present invention relates to a non-electrically powered device comprising:

a) a reservoir chamber having an open end;
b) a non-aqueous active volatile liquid composition containing at least two ingredients;
c) a reservoir chamber lid securely covering the open end of the reservoir chamber, the lid having at least one aperture; and
d) a wick-emanator superstructure securely positioned in the aperture of the reservoir chamber lid. The superstructure includes
   I) an emitting part extending over the reservoir chamber lid and having an evaporative surface exposed to the surrounding air; and
   I) a wicking part extending down through the lid and in submerged contact with the active volatile liquid.

This device is characterized in that i) at least 60% by weight of the non-aqueous active volatile liquid composition comprising ingredients having a vapor pressure of between 4 Pa and 270 Pa;
ii) the emitting part has a weight of between 80 and 1000 grams per square meter of evaporative surface and an absorbency of between 0.01 and 0.1 grams of non-aqueous active volatile liquid composition per square centimeter of evaporative surface; and
iii) less than about 20% by weight of the non-aqueous active volatile liquid composition is absorbed by the emitting part.

The invention device may also consist of only the above-cited elements.

BRIEF DESCRIPTION OF THE DRAWINGS

FIG. 1 represents a composite elevational view of an unassembled wick-emanator superstructure of a first embodiment of the invention devices, the superstructure being obtained by assembling in a star-like shape of two different emitting bodies, 1a and 1b, and a body, 1c, which comprise an emitting body and the wicking part of the wick-emanator superstructure.

FIG. 2 represents an exploded prospective view of an invention device having a wick-emanator superstructure 1, obtained by assembling the bodies of FIG. 1, with an upper emitting part and a lower wicking part, and wherein the wicking part has a form which is complementary with the apertures of the reservoir chamber lid 2, the latter being intended to close the open end of the reservoir chamber 3.

FIG. 5 represents an exploded prospective view of an invention device having a wick-emanator unit 7, obtained by folding body 6 of FIG. 4, with an upper emitting part and a lower wicking part, and wherein the wicking part has a form which is complementary with the apertures of the reservoir chamber lid 8, intended to close the open end of the reservoir chamber 3.

FIG. 6 represents a prospective view of an assembled invention device 4, according to FIG. 5.

DETAILED DESCRIPTION OF THE PREFERRED EMBODIMENTS

Figure 3:
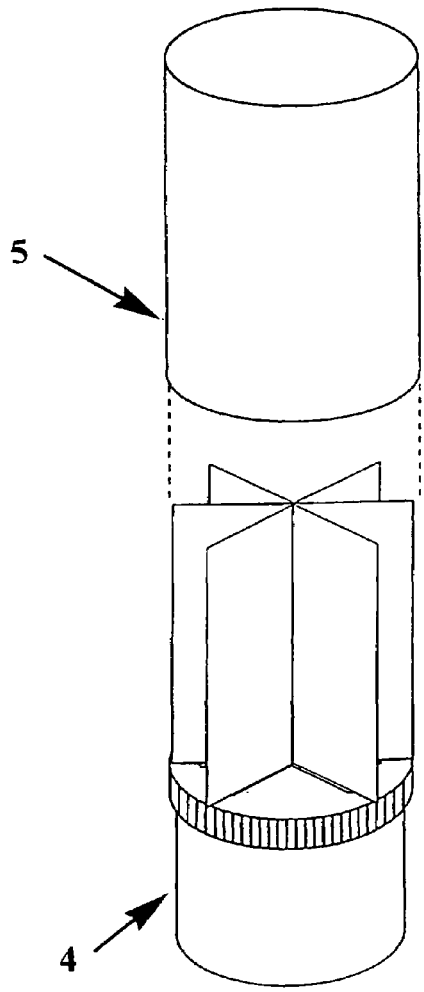
FIG. 3 represents a prospective view of an assembled invention device 4, according to FIG. 2, in proximity to a device closure cap or cover 5.

By the expression "non-electrically powered device" it is meant here a device which is able to release a volatile, with an essentially linear performance over the lifetime of the device, without requiring an electric help such as heating or venting means.

Other means generally used to regulate the rate of evaporation of the active volatile liquid, such as covers or caps allowing regulation the evaporative surface of an emanating body are not mandatory in the invention's devices. Such covering means can be present or not.

Moreover, by "active volatile liquid" we mean here a liquid which is at least partially volatile, i.e. can evaporate, and which is able to impart a benefit to the surrounding space.

The reservoir chamber has the function of storing the non-aqueous active volatile liquid composition, from now on referred to also as "active composition", that is not absorbed by the wick-emanator superstructure.

The reservoir chamber lid has the function of preventing the evaporation of the active composition from the reservoir and also of acting as support of the wick-emanator superstructure.

The reservoir chamber lid securely covers the open end of the reservoir chamber either by acting as, e.g., a screwed stopper or by being permanently sealed to the reservoir chamber.

Preferably the chamber lid has either one or two apertures, for holding the wick-emanator superstructure.

The reservoir chamber, as well as the reservoir chamber lid, are constructed from materials which are compatible with the active composition and totally impermeable to the vapors of the latter. Preferably the reservoir chamber is made of a transparent or translucent material, so that a consumer can visually monitor the level of the active composition, present in the reservoir chamber, and therefore know when the device according to the invention has to be replaced because exhausted.

Suitable materials for the reservoir chamber and the reservoir chamber lid, include injection or thermoform molded materials such as those obtainable from polymers like polyethylene, polypropylene, polystyrene, polyvinyl chloride, polyvinyl acetate, polyamide, polyacrylamide, polymethylacrylate, and the like. Alternatively, the reservoir, or the reservoir and the lid, could be formed from glass.

It is also understood that the reservoir and the lid could be parts of a single body. An example of such body can be a bottle having an open neck, the bottle being the reservoir and the neck being the lid.

By "non-aqueous active volatile liquid composition" it is meant here an active volatile liquid composition which is essentially devoid of or contains only marginal amounts of water, e.g. one may cite as example a composition which contains less than 5%, of it total weight, of water.

A useful active composition is also surfactant free or devoid of the latter.

The active composition contains at least two ingredients. The ingredients can be divided into ingredients capable of imparting a benefit to the surrounding space or enclosed space, and forming an active volatile material, and optional ingredients which can be beneficial to the active volatile material. In other words the active composition contains an active volatile material, comprising at least one ingredient, and optionally one or more ingredients selected from the group consisting of solvents, thickeners, anti-oxidants, dyes, bittering agents and UV inhibitors.

As the active volatile material, there can be used, for example, a perfume, in which case the consumer product will be of the air freshener type. Other suitable active volatile materials can be deodorizing or sanitizing agents or insect repellents or any other active materials capable of imparting perceptible and desirable benefits to the quality of the air into which it is diffused.

Preferred active volatile material is a perfume. As perfume there can be used any ingredient or mixture of ingredients currently used in perfumery, i.e. capable of exercising a perfuming action. More often, however, it will be a more or less complex mixture of ingredients of natural or synthetic origin. The nature and type of the ingredients do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitrites, terpene hydrocarbons, nitrogenous or sulphurous heterocyclic compounds and essential oils of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery.

Although special mention has been made hereinabove of the perfuming effect that can be exerted by the devices of the invention, the same principles apply to analogous devices for the diffusion of deodorizing or sanitizing vapors, the perfume being replaced by a deodorizing composition, an antibacterial, an insecticide, an insect repellent or an insect attractant. By the term "sanitizing vapors", we refer here not only to the vapors of those substances which can enhance the degree of acceptance of the air surrounding the observer, but also to those substances which can exert an attractant or repellent effect towards certain species of insects, for instance towards houseflies or mosquitoes, or else, which can have bactericide or bacteriostatic activity. It goes without saying that mixtures of such agents can also be used.

The total amount of active volatile material in the active composition may be comprised between 20% and 100%, preferably between 30% and 70%, of the weight of the of the active composition.

As anticipated above, the active composition may also contain some optional ingredients acting as, for example, solvents, thickeners, anti-oxidants, dyes, bittering agents and UV inhibitors.

The presence of one or more solvents may be useful to have a single-phase liquid and/or to modulate the speed of evaporation of the active material into the surrounding air. The solvents may belong to the families of isoparaffins, paraffins, hydrocarbons, glycols, glycol ethers, glycol ether esters, esters or ketones.

Examples of commercially available solvents useful to the invention are known under the tradename Isopar® H, J, K, L, M, P or V (isoparaffins; origin: Exxon Chemical), Norpar® 12 or 15 (paraffins; origin: Exxon Chemical), Exxsol® D 155/170, D 40, D 180/200, D 220/230, D 60, D 70, D 80, D 100, D 110 or D 120 (dearomatised Hydrocarbons; origin: Exxon Chemical), Dowanol® PM, DPM, TPM, PnB, DPnB, TPnB, PnP or DPnP (glycol ethers; origin: Dow Chemical Company), Eastman® EP, EB, EEH, DM, DE, DP or DB (glycol ethers; origin: Eastman Chemical Company), Dowanol® PMA or PGDA (glycol ether esters; origin: Dow Chemical Company) or Eastman® EB acetate, Eastman® DE acetate, Eastman® DB acetate, Eastman® EEP (all glycol ether esters; all origin: Eastman Chemical Company).

Other examples of solvents useful to the invention are dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

The total amount of solvents present in the active composition may vary between 0.0% and 80%, preferably between 30% and 70%, the percentages being relative to the weight of the active composition.

As non-limiting examples of useful thickener ingredients, one can cite ethyl cellulose (commercial examples of which are available from Hercules Inc.), fumed silica (commercial examples of which are available from Degussa) and styrene-butadiene-styrene block copolymers (commercial examples of which are available from Shell).

The total amount of thickeners present in the active composition may vary between 0.0% and 10%, preferably between 1% and 4%, the percentages being relative to the weight of the active composition.

As non-limiting examples of useful antioxidant ingredients, one can cite the sterically hindered amines, i.e. the derivatives of the 2,2,6,6-tetramethyl-piperidine, such as those known under the tradename Uvinul® (origin BASF AG) or Tinuvin® (origin: Ciba Speciality Chemicals), as well as the alkylated hydroxyarene derivatives, such as butylated hydroxytoluene (BHT).

The total amount of antioxidants present in the active composition may vary between 0.0% and 10%, preferably between 1% and 4%, the percentages being relative to the weight of the active composition.

Dyes are other optional ingredients of the active composition. Suitable dyes are oil-soluble and can be found in the Colour Index International, published by The Society of Dyers and Colourist. Non-limiting examples of suitable dyes are derivatives of the anthraquinone, methine, azo, triarylmethane, triphenylmethane, azine, aminoketone, spirooxazine, thioxanthene, phthalocyanine, perylene, benzopyran or perinone families. Examples of such dyes which are commercially available are known under the tradename Sandoplast® Violet RSB, Violet FBL, Green GSB, Blue 2B or Savinyl® Blue RS (all anthraquinone derivatives; origin: Clariant Huningue S.A.), Oilsol® Blue DB (anthraquinone; origin: Morton International Ltd.), Sandoplast® Yellow 3G (methine; origin: Clariant Huningue S.A.), Savinyl® Scarlet RLS (azo metal complex; origin: Clariant Huningue S.A.), Oilsol® Yellow SEG (monoazo; origin: Morton International Ltd.), Fat Orange® R (monoazo; origin: Hoechst AG), Fat Red® 5B (diazo; origin: Hoechst AG), Neozapon® Blue 807 (phtalocyanine; origin: BASF AG), Fluorol® Green Golden (perylene; origin: BASF AG).

The total amount of dyes present in the active composition may vary between 0.0% and 0.5%, preferably between 0.005% and 0.05%, the percentages being relative to the weight of the active composition.

The presence of a bittering agent may be desirable in order to render the product unpalatable, making less likely that the active composition is ingested, especially by young children. One can cite, as non-limiting example, isopropyl alcohol, methyl ethyl ketone, methyl n-butyl ketone or yet a denatonium salt such as the denatonium benzoate known also under the trademark Bitrex™ (origin: Mac Farlan Smith Ltd.).

The bittering agent may be incorporated in the active composition in a total amount comprised between 0.0% and 5%, the percentages being relative to the total weight of the active composition. In the case of Bitrex™ the amount can be comprised between 0.0% and 0.1%, preferably between 0.001% to 0.05% of the total weight of the active composition.

As non-limiting examples of useful UV-inhibitor ingredients, one can cite benzophenones, diphenylacrylates or cinnamates such as those available under the trade name Uvinul® (origin: BASF AG).

The total amount of UV-inhibitors present in the active composition may vary between 0.0% and 0.5%, preferably between 0.01% and 0.4%, the percentages being relative to the total weight of the active composition.

As mentioned above, at least 60% by weight of the active composition comprises ingredients having a vapor pressure comprised between 4 Pa and 270 Pa, the vapor pressure being measured at 20° C. and a pressure of 760 mmHg. The described requirement in the formulation of the active composition ensures that a relatively constant composition is maintained over the lifetime of the device and that the active composition evaporates at a relatively steady rate during the life of the product.

Most preferably, at least 80% by weight of the active composition comprises ingredients having a vapor pressure comprised between 4 Pa and 270 Pa.

The device of the invention also comprises a wick-emanator superstructure that consist of an emitting part and a wicking part.

The emitting part and the wicking parts can be separated entities contacting each to other to form the superstructure or can be a single entity.

Moreover, the emitting part may comprise one or more emitting bodies in contact to each other, in general from one to four emitting bodies are used. Similarly, the wicking part may comprise one or more wicks, in general from one to four wicks are used.

The emitting part contributes more than significantly to the regulation of the speed of evaporation of the active composition. Indeed, thanks to its specific absorbency, its weight per square meter of evaporative surface and optionally its evaporative surface, the emitting part is able to influence the evaporation of the active composition so that the evaporation occurs at an essentially constant rate during the lifetime of the device.

By "rate" it is meant here the amount of active composition, per unit of time, which is emitted into the surroundings during a given frame of time, or if preferred a weight loss per a given period of time.

By "essentially constant rate" it is meant here a rate which can oscillate in a range comprised between approximately 80% and approximately 120% of the mean rate, preferably between 90% and 110%, during a period of at least 20 days, or even 25 days, of use of the invention's device.

As mentioned above, the emitting part has the capacity of absorbing from 0.01 g to approximately 0.1 g of active composition per square centimeter of evaporative surface, and has a weight comprised between 80 g/m$^2$ and 1000 g/m$^2$, relative to the evaporative surface. Moreover, the emitting part absorbs less than about 20% of the initial total weight of active volatile liquid present in device.

Preferably the emitting part has the capacity to absorb from 0.02 g to approximately 0.08 g of active volatile liquid per square centimeter of evaporative surface, and has a weight comprised between 100 g/m² and 500 g/m², relative to the evaporative surface. Furthermore, the emitting part preferably absorbs less than about 15% of the initial total weight of active volatile liquid present in device.

The emitting part can also be characterized by an evaporative surface comprised between 50 cm² and 200 cm². Preferably, the evaporative surface will be comprised between 100 cm² and 150 cm².

Non-limiting examples of materials of which the emitting part can be made are cellulose derivatives, e.g. papers, molded ceramics, sintered or porous plastics.

Preferred papers are those currently used as filter paper and having a particle retention size comprised between 3 µm and 30 µm, such as those commercially available from Whatman International Ltd., UK as Filter Paper N° 1, 3, 4 or 113.

In the case of sintered or porous plastics, preferably the material will have a porous size comprised between 5 µm and 200 µm and is based on high density polyethylene, ultra high molecular weight polyethylene or polypropylene. Examples of such materials are commercially available, e.g., under the tradename Vyon® T (origin: Porvair Technology Ltd, UK).

The wicking part is intended to absorb a part of the active composition and transport the latter to the emitting part, from which it can evaporate into the surrounding space of the invention's device. As mentioned previously, the wicking part may comprise between one and four wicks.

The wicking part may be made of organic and inorganic materials. Examples for appropriate inorganic materials include porous porcelain materials, molded ceramics, glass fibers, or asbestos, in combination with a suitable binder such as, for example, gypsum or bentonite. It is also possible to prepare wicks from powdered mineral materials, such as, for example, clay, talc, kieselguhr, alumina, silica or the like, singly or in combination with, for example, wood flour, carbon powder, or activated carbon, using an appropriate glue. Organic materials include felt, cotton, pulp, woven and non-woven cotton fibers, synthetic fibers, cellulose derivatives, e.g. papers, and woven and non-woven sintered or porous plastics. Preferably, the wicking part and the emitting part are made of the same material.

As anticipated above, a consumer article may comprise a device of the invention. Such a consumer article can be, depending on the nature of the active composition used, in the form of a perfuming or sanitizing device such as an air freshener, a car freshener, a closet freshener, an insecticide or an insect repellent device or a combination thereof if it is used an active composition capable of exerting more that one effect, e.g. a perfuming and sanitizing effect. Air-fresheners are a preferred embodiment of the invention's devices.

During the storage of the invention's device, the active composition may be prevented from evaporating through a variety of methods.

For instance, if the consumer product comprises a fully assembled invention device, a first method to prevent the evaporation of active volatile liquid may consist in using a sealing which covers the emitting part of the device thus preventing the evaporation of the active composition prior to activation by a consumer.

Alternatively, if the consumer product comprises an unassembled invention device, e.g. wherein the wick-emanator superstructure is not fixed to the rest of the device, then another method to prevent the evaporation of active volatile liquid may consist in sealing the apertures of the reservoir chamber lid. In such a case the device will be activated by the consumer simply by removing the sealing and introducing the wicking part of the wick-emanator superstructure into the lid apertures.

Furthermore, if the consumer product comprises an unassembled invention device, e.g. wherein the emitting part is not fixed to the rest of the device such as when the wicking part and the emitting part are separate bodies, then to prevent the evaporation of active volatile liquid it is possible to seal the wicking part extending over the lid. The consumer will activate such a device simply by removing the sealing and locating the emitting part such as that it is in direct contact with the wicking part.

The sealing mentioned above can be a removable and vapor-impermeable closure cap, cover or film.

The combination of the invention device and of a closure cap, cover or film may constitute a consumer article which is a further object of the present invention.

It is also interesting to note that the consumer article according to the invention once exhausted may be easily reactivated by the consumer simply by refilling the reservoir chamber with an active volatile liquid, which may be provided in separated sachets.

Furthermore, another object of the invention is a kit for the preparation of a device as defined above, the kit comprising a reservoir chamber, a reservoir chamber lid and a wick-emanator superstructure as defined in claim 1. In the embodiment an active composition as defined above can be supplied separately to the consumer.

Alternatively, the kit may further comprise the active composition, which is either contained in the reservoir, which is sealed, or the kit comprises also a containing means, or a plurality of the containing means, filled with the active composition.

In the embodiment of the invention, all the various element of the invention's device can be in a non-assembled or partially assembled form, for example as described above.

EXAMPLES

The following examples are further illustrative of the present invention embodiments, and further demonstrate the advantages of the invention devices relative to prior art teachings.

Example 1

An air freshener dispenser in accordance with the present invention was constructed as illustrated in FIGS. 1 to 3. The bodies 1a, 1b and 1c, having the dimension given in FIG. 1, were cut from a sheet of 2 mm thick Vyon T® (Porvair Technology Ltd.), and assembled to form a wick-emanator superstructure 1, as pictured in FIG. 2. Reservoir chamber lid 2 was provided with an aperture to accept the wick-emanator superstructure 1. A reservoir chamber 3, see FIG. 2, having approximately a volume of 30 ml was filled with 10 g of a perfuming composition and 10 g of dipropylene glycol n-butyl ether (Dowanol® DPnB, origin: Dow Chemical Company). After assembling the filled reservoir, the lid and the wick-emanator superstructure it was obtained a device according to the invention as shown in FIG. 3. The total mass of device was recorded. The device was placed in a temperature-humidity controlled test room (at 20° to 22° C. and 45% to 55% relative humidity) and the weights recorded at regular intervals up to 45 days. The test data are listed in Table I.

TABLE I

Evaporation of the active liquid volatile component as a function of time

| Elapsed time (t) (days) | Cumulative weight loss (cwl) (g) | Rate of evaporation* (g/day) |
|---|---|---|
| 0.00 | 0.00 | |
| 10.00 | 5.12 | 0.51 |
| 13.95 | 6.43 | 0.33 |
| 17.81 | 7.71 | 0.33 |
| 23.76 | 9.72 | 0.34 |
| 29.71 | 11.62 | 0.32 |
| 30.98 | 12.04 | 0.33 |
| 35.95 | 13.56 | 0.31 |
| 41.93 | 15.41 | 0.31 |
| 45.93 | 16.36 | 0.31 |

*calculated by applying the following formula: $(cwl_{t_2} - cwl_{t_1})/(t_2 - t_1)$ Table I shows that an invention device emanates a high volume of vapor (up to 75% of the whole volatile in 45 days) with a very uniform rate over at least 32 days of use and without requiring any external input such an electrical heater.

Composition of the perfuming composition used in this example

| Ingredients | Parts by weight |
|---|---|
| Mixture of nonyl acetate and 2-methyloctyl acetate | 2.21 |
| Benzyl acetate | 2.94 |
| Citronellyl acetate | 1.47 |
| Phenylethyl acetate | 2.94 |
| (Z)-3-Hexen-1-ol acetate | 1.10 |
| Prenyl acetate | 0.37 |
| Ethyl acetoacetate | 27.21 |
| 9-Undecenal | 0.15 |
| Anethole | 0.37 |
| Ethyl-2-methylvalerate | 0.22 |
| 4-Undecanolide | 2.21 |
| Damascenia 185 SA[1] | 0.37 |
| Dihydromyrcenol | 2.94 |
| Dipropyleneglycol monomethyl ether | 41.93 |
| Dynascone ®[2] | 0.07 |
| Habanolide ®[3] | 0.59 |
| Hedione ® HC[4] | 1.76 |
| 10%** Indol | 0.29 |
| Iralia ® total[5] | 1.10 |
| Isoeugenol | 0.29 |
| 6-Methoxy-2,6-dimethylheptanal | 0.07 |
| Oxane[6] | 0.29 |
| 3,6-Dihydro-4,6-dimethyl-2-phenyl-2H-pyran | 0.07 |
| 1%* Nonadienal | 0.22 |
| (Z)-3-Hexen-1-ol | 1.10 |
| Polysantol ®[7] | 0.44 |
| Pipol salicylate | 2.21 |
| Orange terpenes | 1.47 |
| Verdox ®[8] | 2.50 |
| Triplat[9] | 1.10 |
| Total | 100.00 |

*in dipropyleneglycol
**in isoparaffin
[1] Compounded perfumery base; origin: Firmenich SA, Geneva, Switzerland
[2] 1-(5,5-Dimethyl-cyclohexen-1-yl)-4-penten-1-one; origin: Firmenich SA, Geneva, Switzerland
[3] Oxacyclohexadecen-2-one; origin: Firmenich SA, Geneva, Switzerland
[4] Methyl 3-oxo-2-pentyl-cyclopentaneacetic acid origin: Firmenich SA, Geneva, Switzerland
[5] Methyl Ionone; origin: Firmenich SA, Geneva, Switzerland
[6] Cis-2-methyl-4-propyl-1,3-oxathiane; origin: Firmenich SA, Geneva, Switzerland
[7] 3,3-Dimethyl-5-(2,2,3-trimethyl-3-cyclopenten-1-yl)-4-penten-2-ol; origin: Firmenich SA, Geneva, Switzerland
[8] 2-Tert-butyl-1-cyclohexyl acetate; origin: IFF, USA
[9] 2,4-Dimethyl-3-cyclohexen-1-carboxaldehyde; origin: IFF, USA Example 2

Figure 4:
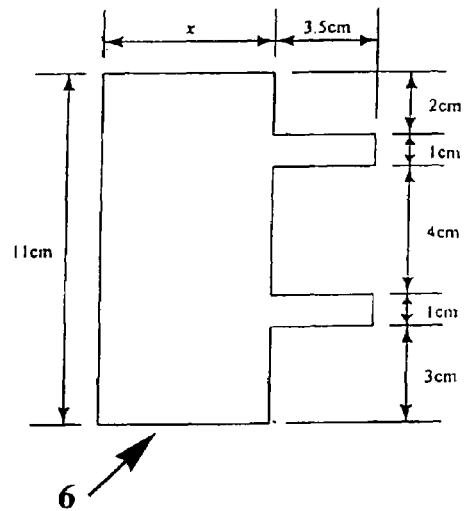
FIG. 4 represents an elevational view of an unassembled wick-emanator superstructure of a second embodiment of the invention devices, the superstructure being composed of one entity 6, which is subsequently folded and sealed in a cylinder-like shape, as pictured in FIG. 5.

Air freshener dispensers in accordance with the present invention were constructed as illustrated in FIGS. 4 to 6. A wick-emanator superstructure 7, according to the one illustrated in FIG. 5, was formed from a single sheet 6, see FIG. 4, made of Whatman No. 4 qualitative filter paper (Whatman Plc). Reservoir chamber lid 8 was provided with apertures to accept the wick-emanator superstructure 7. A reservoir chamber 3, see FIG. 5, having approximately a volume of 30 ml was filled with 10 g of the perfuming composition used in example 1 and 10 g of dipropylene glycol n-butyl ether (Dowanol® DPnB, origin: Dow Chemical Company). After assembling the filled reservoir, the lid and the wick-emanator superstructure it was obtained a device according to the invention as shown in FIG. 6. Four devices having the emitting part with different surface areas (SA) were built using the same protocol as above. The total mass of each device was recorded. The devices were placed in a temperature-humidity controlled test room (at 20° to 22° C. and 45% to 55% relative humidity) and the weights recorded at regular intervals up to 47 days. The test data are listed in Table II.

TABLE II

Evaporation of the active liquid volatile component as a function of time

| Elapsed time (t) (days) | Cumulative weight loss (cwl) (g) | | | |
|---|---|---|---|---|
| | SA = 50 cm² | SA = 100 cm² | SA = 150 cm² | SA = 200 cm² |
| 0.00 | 0.00 | 0.00 | 0.00 | 0.00 |
| 4.73 | | | | 2.57 (0.54) |
| 7.08 | | | 2.79 (0.39) | 3.61 (0.44) |
| 8.79 | | | 3.27 (0.28) | 4.30 (0.41) |
| 11.81 | 1.56 (0.13) | 2.87 (0.24) | 3.90 (0.21) | 5.19 (0.30) |
| 13.73 | 1.85 (0.15) | 3.25 (0.20) | 4.44 (0.29) | 6.00 (0.42) |
| 15.94 | 2.25 (0.18) | 3.77 (0.23) | 5.07 (0.29) | 7.00 (0.45) |

TABLE II-continued

Evaporation of the active liquid volatile component as a function of time

| Elapsed time (t) (days) | Cumulative weight loss (cwl) (g) | | | |
|---|---|---|---|---|
| | SA = 50 cm² | SA = 100 cm² | SA = 150 cm² | SA = 200 cm² |
| 21.04 | 3.01 (0.15) | 4.68 (0.18) | 6.45 (0.27) | 8.94 (0.42) (0.38) |
| 29.82 | 4.37 (0.16) | 6.29 (0.18) | 9.17 (0.31) | 12.15 (0.37) |
| 34.92 | 5.04 (0.13) | 7.19 (0.18) | 10.27 (0.21) | 13.87 (0.34) |
| 41.06 | 5.94 (0.15) | 8.17 (0.16) | 11.76 (0.24) | 15.36 (0.24) |
| 47.71 | 6.91 (0.15) | 9.25 (0.16) | 13.21 (0.22) | 16.92 (0.23) |

Values between brackets represents the rate of evaporation (g/day) calculated as in example 1.

As in Example 1, these invention devices, although having an emitting part with a different shape or surface, emanates a high volume of vapor with a very uniform rate without requiring any external input such an electrical heater or a fan.

What is claimed is:

1. A non-electrically powered device comprising:
   a) a reservoir chamber having an open end;
   b) a non-aqueous active volatile liquid composition containing at least two ingredients;
   c) a reservoir chamber lid securely covering the open end of the reservoir chamber, the lid having at least one aperture; and
   d) a wick-emanator superstructure securely positioned in the aperture of the reservoir chamber lid, the superstructure including:
      I) an emitting part extending over the reservoir chamber lid and having an evaporative surface exposed to the surrounding air; and
      II) a wicking part extending down through the lid and in submerged contact with the active volatile liquid;
   with
   i) at least 60% by weight of the non-aqueous active volatile liquid composition comprising ingredients having a vapor pressure of between 4 Pa and 270 Pa;
   ii) the emitting part having a weight of between 80 and 1000 grams per square meter of evaporative surface and an absorbency of between 0.01 and 0.1 grams of non-aqueous active volatile liquid composition per square centimeter of evaporative surface; and
   iii) less than about 20% by weight of the non-aqueous active volatile liquid composition is absorbed by the emitting part.

2. The device according to claim 1, wherein the evaporative surface of the emitting part is between 50 cm² and 200 cm².

3. The device according to claim 1, wherein the non-aqueous active volatile liquid composition contains an active volatile material and optionally one or more ingredients selected from the group consisting of solvents, thickeners, anti-oxidants, dyes, bittering agents and UV inhibitors.

4. The device according to claim 3, wherein the active volatile material is selected from the group consisting of perfumes, deodorizing or sanitizing agents and insect repellents.

5. The device according to claim 3, wherein the amount of active volatile material is between 20% and 100% of the weight of the non-aqueous active volatile liquid composition.

6. The device according to claim 1, wherein at least 80% by weight of the non-aqueous active volatile liquid composition comprises ingredients having a vapor pressure of between 4 Pa and 270 Pa.

7. The device according to claim 1, wherein the emitting part has a weight of between 100 g/m² and 500 g/m², relative to the evaporative surface, and has an absorbency of between 0.02 and 0.08 grams of non-aqueous active volatile liquid composition per square centimeter of evaporative surface; and the emitting part absorbs a quantity of non-aqueous active volatile liquid composition that is less than about 15% of the initial total weight of the non-aqueous active volatile liquid composition present in the device.

8. The device according to claim 7, wherein the emitting part and the wicking part are made of the same material.

9. A consumer article, comprising a device according to claim 1.

10. The consumer article according to claim 9 in the form of a perfuming or sanitizing device, an air freshener, a car freshener, a closet freshener, an insecticide or an insect repellent device or a combination thereof.

11. The consumer article according to claim 10 in the form of an air freshener.

12. The consumer article according to claim 9 further comprising a closure cap, cover or film.

* * * * *